US00PP20059P2

(12) United States Plant Patent
Egger

(10) Patent No.: US PP20,059 P2
(45) Date of Patent: Jun. 2, 2009

(54) ***PULMONARIA* PLANT NAMED 'SILVER BOUQUET'**

(50) Latin Name: *Pulmonaria*
Varietal Denomination: Silver Bouquet

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 58 days.

(21) Appl. No.: 12/077,334

(22) Filed: Mar. 18, 2008

(51) Int. Cl.
*A01H 5/00* (2006.01)

(52) U.S. Cl. ..... Plt./473

(58) Field of Classification Search ..... Plt./473
See application file for complete search history.

*Primary Examiner*—Annette H Para
(74) *Attorney, Agent, or Firm*—Klarquist Sparkman, LLP

(57) ABSTRACT

A new and distinct hybrid of *Pulmonaria* plant characterized by dark pink flowers, medium flower size, foliage with prominent silvering, a medium compact habit, excellent vigor, and excellent tolerance to mildew.

1 Drawing Sheet

Botanical denomination: *Pulmonaria* hybrid.
Variety designation: 'Silver Bouquet'.
Parentage: *Pulmonaria longifolia* ssp. *cevennensis*×*Pulmonaria saccarata.*

BACKGROUND OF THE INVENTION

The present invention relates to a new and distinct cultivar of *Pulmonaria* and given the cultivar name of 'Silver Bouquet'. *Pulmonaria* is in the family *Boraginaceae*. The new cultivar originated as a seedling from PU-00-23, an unpatented experimental plant that originated from a cross between *Pulmonaria longifolia* ssp. *cevennensis,* as the seed parent, and *P. saccharata,* as the pollen parent. The plant was in an experimental field surrounded by proprietary clones of mostly hybrids of *P. saccharata* ×*P. longifolia.* The plant was open pollinated, the plant was bagged, and the seedlings were grown and evaluated. This new cultivar was selected for its heavy silvering, mildew tolerance, compact habit, and medium sized pink flowers.

SUMMARY OF THE INVENTION

This new *Pulmonaria* is distinguished by:

1. dark pink flowers;
2. medium flower size;
3. foliage with prominent silvering;
4. medium, compact habit;
5. excellent vigor and mildew tolerance.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg. shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows the summer foliage and habit of *Pulmonaria* 'Silver Bouquet'.

FIG. 2 shows the new variety in flower in the spring, growing in the ground in Canby, Oreg.

DETAILED PLANT DESCRIPTION

The following is a detailed description of the new *Pulmonaria* hybrid based on observations of two-year-old specimens grown in the ground in full sun under typical outdoor conditions in the trial fields in Canby, Oreg. Canby is Zone 8 on the USDA Hardiness map. Temperatures range from a high of 95 degrees F. in August to an average of 32 degrees F. in January. Normal rainfall in Canby is 42.8 inches per year.

The color descriptions are all based on The Royal Horticultural Society Colour Chart.

Plant:
- *Type.*—Herbaceous perennial.
- *Hardiness.*—USDA Zones 5 to 9.
- *Spring size.*—45 cm wide and 25 cm tall.
- *Summer size.*—38 cm wide and 25 cm tall.
- *Form.*—Clumping.
- *Vigor.*—Excellent.
- *Roots.*—Thickened, fleshy, white; propagates easily from crown divisions.

Leaf:
- *Type.*—Simple.
- *Shape.*—Oblanceolate.
- *Arrangement.*—Rosette.
- *Blade length.*—Grows to 28 cm long.
- *Blade width.*—7 cm at widest point.
- *Margins.*—Slightly undulate.
- *Apex.*—Acuminate.
- *Base.*—Attenuate.
- *Venation.*—Pinnate.
- *Surface texture.*—Scabrous and sparingly glandular on both sides.

*Petiole description.*—12 cm to 16 cm, scabrous and sparingly glandular, Yellow Green 146A near blade and Greyed Purple 187A near base.

*Color.*—Topside silver, Greyed Green 194B with deep green, Green 137A, occasional blotches along edges; bottom side closest to Yellow Green 147C.

Cauline Leaves: (These are found in the spring only on the flowering stems. After the seed is produced these stems die out.):

*Type.*—Simple.

*Arrangement.*—Alternate.

*Shape.*—Oblanceolate to ovate.

*Length.*—Variable, 4 cm to 10 cm.

*Width.*—3 cm.

*Margins.*—Entire.

*Apex.*—Acuminate.

*Base.*—Clasping, sessile.

*Leaf texture.*—Hispid.

*Venation.*—Pinnate.

*Color.*—Topside Greyed Green 194B with margins and blotches of Yellow Green 147A; bottom side closest to Yellow Green 147B.

Inflorescence:

*Type.*—Terminal forked cyme.

*Number of flowers per cyme.*—12 to 37.

*Number of inflorescences in first spring flush.*—71.

*Peduncle.*—17 cm long, 4 mm wide, hispid.

*Color.*—Yellow Green 145B to Greyed Brown 199A in more light.

*Pedicel.*—2 mm to 5 mm long, hispid, Brown 200B.

Flower Bud:

*Size.*—6 mm long and 5 mm wide where extrudes from calyx.

*Shape.*—Ovoid.

*Color.*—Red Purple 60C.

Flower:

*Type.*—Actinomorphic.

*Corolla description.*—Funnelform, 1.8 cm deep and 1.5 cm wide; 5 fused petals with rounded lobes; lobes entire, obtuse; color changes with age from Red Purple 60C on both surfaces to Red Purple 63C with tints of Purple 77A.

*Calyx description.*—5 fused sepals, 1.5 cm deep and 6 mm wide, tubular campanulate, parted ¼ to base, entire, tips acute, hispid, outside color closest to Brown 200A, inside color between Brown 200A and Yellow Green 147B.

*Pistil description.*—One, 7 mm long, ovary 1 mm deep, Yellow Green 144A, style 6 mm long, thrum type, inserted in the corolla tube, Yellow Green 144D, stigma Yellow Green 144D.

*Stamen description.*—Anthers 5 in number, attached to and inserted in the top of tube, Greyed Purple 187A, 2 mm long; pollen White 155A.

*Bloom period.*—April to May in Canby, Oreg.

*Fragrance.*—None.

Seed:

*Type.*—4 smooth nutlets, Black 202A and shiny, typical of the genus.

*Fertility.*—Low.

Pest and Diseases: No powdery mildew has developed on this new variety. Mildew is a common problem of *Pulmonaria. Pulmonaria longifolia* ssp. *cevennensis* is one of the few *Pulmonaria* sp. that does not have major mildew problems. Snails and slugs could be a problem.

Comparisons to Similar *Pulmonaria:*

Compared to *Pulmonaria longifolia* spp. *cevennesis,* one of the parent species, the new variety has dark pink rather than pink to blue flowers and leaves that are larger and much more silver in color.

Compared to *Pulmonaria* 'Silver Shimmers', (U.S. Plant Pat. No. 13,290), *Pulmonaria* 'Silver Bouquet' has dark pink colored flowers rather than blue violet. The flowers are smaller. Their habits and leaf colorations are similar.

Compared to *Pulmonaria* 'Moonshine' (U.S. Plant Pat. No. 13,686), the new variety has longer leaves and dark pink rather than very light violet blue almost white flowers.

I claim:

1. A new and distinct hybrid of *Pulmonaria* plant as herein illustrated and described.

* * * * *

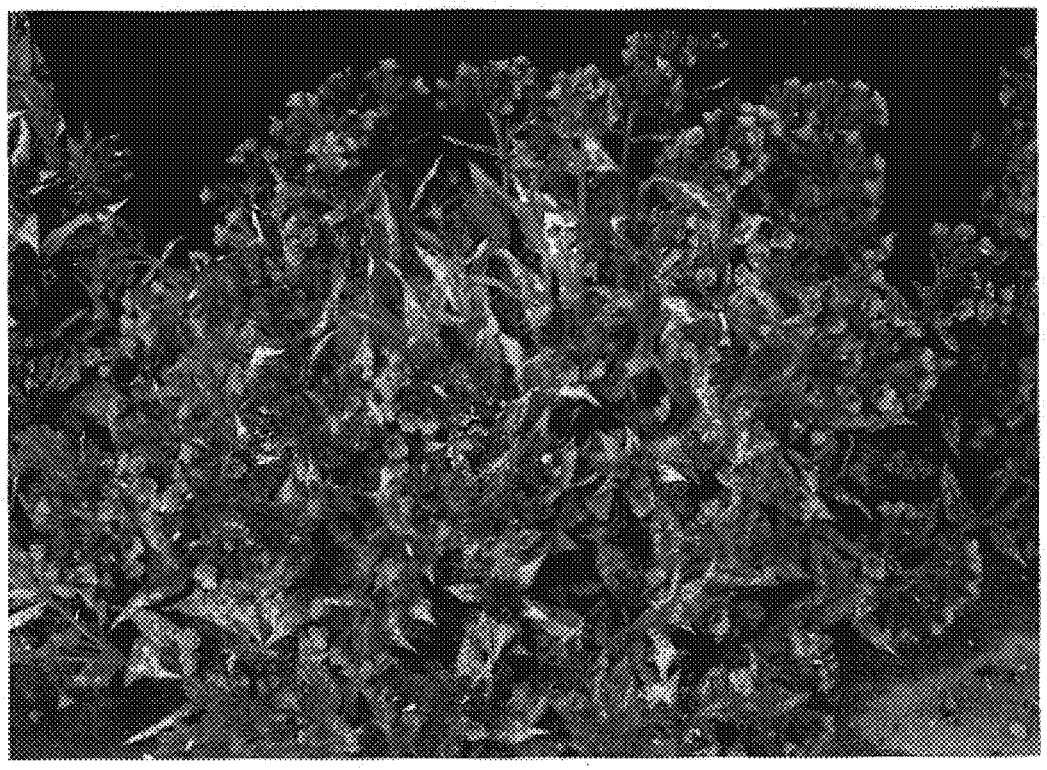

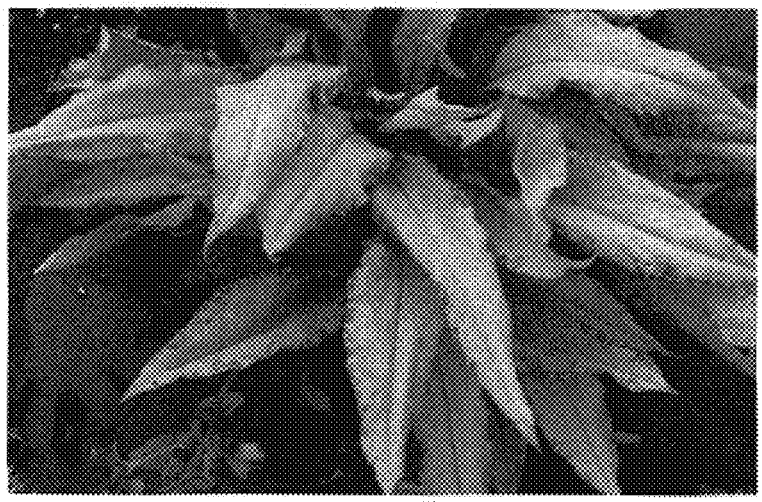
Figure 1 above, figure 2 below